United States Patent [19]

Harris

[11] Patent Number: 4,711,027
[45] Date of Patent: Dec. 8, 1987

[54] IMPLANTABLE LEAD CONSTRUCTION
[75] Inventor: Donald L. Harris, Key Largo, Fla.
[73] Assignee: Cordis Corporation, Miami, Fla.
[21] Appl. No.: 892,959
[22] Filed: Aug. 4, 1986

Related U.S. Application Data

[63] Continuation-in-part of Ser. No. 672,334, Nov. 16, 1984, Pat. No. 4,627,439, which is a continuation-in-part of Ser. No. 561,648, Dec. 15, 1983, Pat. No. 4,567,901.

[51] Int. Cl.$^4$ ............................................. H01R 43/00
[52] U.S. Cl. ........................................ 29/869; 29/857; 128/419 D; 128/419 P; 128/785; 174/84 R
[58] Field of Search ................. 29/447, 857, 869, 868; 128/419 P, 419 D, 785, 788; 174/84 R

[56] References Cited
U.S. PATENT DOCUMENTS

2,742,622 4/1956 Stevens, Jr. .
3,634,924 1/1972 Blake et al. .
3,668,778 6/1972 Lindtvelt et al. .
4,419,819 12/1983 Dickhudt et al. .

Primary Examiner—Howard N. Goldberg
Assistant Examiner—Carl J. Arbes
Attorney, Agent, or Firm—Lockwood, Alex, Fitzgibbon & Cummings

[57] ABSTRACT

A method is provided for constructing a mechanically strong and fluid tight assembly of an electrode along the length of an implantable lead, such as those leads suitable for cardiac pacing and diagnosis and the like. In the preferred embodiment, a short annular sheath polymeric tube is closely positioned over a coiled insulated conductor, an electrode is positioned over the short annular sheath, and a section of the insulating sheath of the lead is positioned over a flange of the electrode and sealed to a shape that is substantially isodiametric with the electrode surface.

23 Claims, 21 Drawing Figures

IMPLANTABLE LEAD CONSTRUCTION

DESCRIPTION

BACKGROUND AND DESCRIPTON OF THE INVENTION

This is a continuation-in-part of application Ser. No. 672,334, filed Nov. 16, 1984, now U.S. Pat. No. 4,627,439 issued 12/9/86 which is a continuation-in-part of application Ser. No. 561,648, filed Dec. 15, 1983 now U.S. Pat. No. 4,567,901 issued 12/9/86.

This invention generally relates to the construction of electrical leads for uses such as cardiac pacing and diagnosis. The invention more particularly relates to a method for constructing implantable leads that are flexible yet possess exceptional fatigue resistance in response to the flexing or bending thereof that occurs during implantation and with the constant movement associated with each ventricular or atrial contraction. The method includes providing a radially recessed annular sheath overlying a coiled conductor, wrapping a portion of the coiled conductor and contacting an uninsulated portion thereof with an electrode such as a ring electrode in order to thereby form an electrode assembly of a lead that has the requisite flexibility and fatigue resistance while being substantially isodiametric with the flexible insulating sheath of the lead.

Leads that are adapted to be implanted within the body of a patient, particularly a cardiac patient, carry electrical pulses from a cardiac pacer or the like to the muscle to be stimulated and also from that muscle in order to transmit cardiac electrical activity to the cardiac pacer or the like. Leads of this type are implanted during major surgical procedures or by threading pervenous leads through appropriate veins and to the heart cavity or the like. Such leads incorporate electrodes for transmitting electrical signals between the live muscle and a conductor within an insulating sheath that substantially connects the electrode to the pacing device or the like which is at a location outside of or subcutaneous of the body. Often these electrodes are so-called ring electrodes which have a generally cylindrical outside surface. It is usually desirable that such outside surface of the electrode be of substantially the same size as and isodiametric with the outside surface of the lead's elongated insulating sheath. Typically, a single or double electrode lead would be useful in conjunction with pacing a single muscle or cardiac chamber, while another one or two electrodes could be added when dual muscle or chamber pacing or the like is to be practiced. Additional numbers of electrodes can be utilized for procedures such as mapping of cardiac tissue. Electrode assemblies should have the ability to remain fully assembled and leak resistant during constant flexing or bending such as is encountered with each ventricular or atrial contraction of cardiac tissue within which such a lead may be implanted. Flexibility is also required in order to avoid penetration of cardiac muscle and the like.

When multiple electrodes are required, a multifilar coil having a plurality of helically coiled conductor wires can be used, one such wire being needed for each electrode. Each coiled conductor must be assembled to each electrode in such a manner as to provide an electrical connection that will not be disturbed during extensive use, and each such electrode assembly should integrate the surrounding insulating sheath therein in a manner that will withstand many years of implantation or use within an environment of body fluids without experiencing the development of leaks in or separations of the electrode assembly.

With particular reference to dual-chamber pacing, such carries out pacing in either or both of an atrium and/or a ventricle of the heart. In some implantation procedures, access is gained through a cephalic vein or an external jugular vein. It is advantageous to avoid two separate incisions to provide access to the vein both for the conductors and for each introducer device therefor, and pacer leads have been developed by which two electrodes can be inserted through the same vein, for example including the use of introducing sheaths that are inserted through a single incision and into the same vein for eventual passage into different heart chambers. Leads that have portions of enlarged diameter have the disadvantage that the vein through which the lead is passed must be able to accommodate the largest diameter of the lead, thereby substantially offsetting the advantage gained by having an otherwise thin lead.

By the present invention, it is possible to construct leads that have a single electrode or a large number of electrodes positioned along a lead, with each such electrode being part of an assembly that includes a portion of the flexible insulating sheath of the electrode lead. Each electrode assembly is constructed by positioning a flexible insulating sheath over an elongated conductor, providing a short annular sheath that fits over the conductor and has a smaller diameter than the flexible insulating sheath, and positioning an electrode member over the short annular sheath. The electrode member is secured in firm electrical contact with an uninsulated portion of the conductor, and the flexible insulating sheath is heat reformed so as to be substantially isodiametric with the external surface of the electrode member.

It is accordingly a general object of the present invention to provide an improved electrode assembly for leads used in cardiac pacing, diagnosis and the like.

Another object of this invention is to provide an improved method for assembling electrodes onto leads for cardiac pacing and diagnosis and the like, which method combines a ring electrode, the insulation of the lead, a conductor, and a sheath overlying the conductor into an exceptionally secure assembly.

Another object of this invention is to provide an improved prebent lead for cardiac pacing and diagnosis which has an external diameter that is substantially constant throughout the length thereof while including a section exhibiting a greater degree of stiffness than other portions of the lead.

Another object of this invention is to provide an improved small diameter pacing and/or mapping lead having high tensile strength and good moisture resistance.

These and other objects of the present invention will become apparent from the following detailed description thereof, taken in conjunction with the accompanying drawings, wherein:

Figures 1, 2, 3, 4:
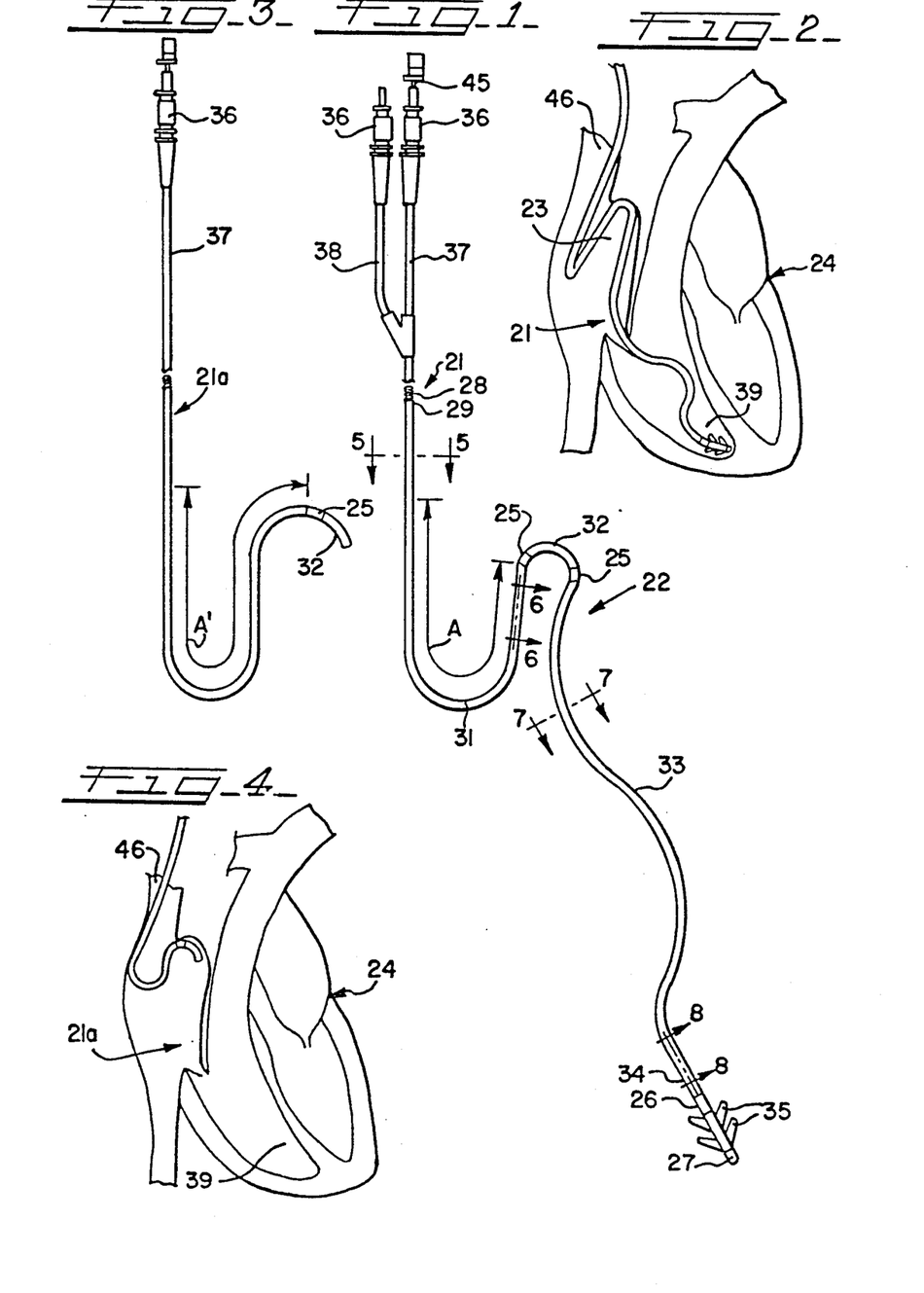
FIG. 1 is an elevational view of a prebent or preshaped ventricular-atrial lead made according to the method of this invention and shown in its molded, relaxed condition.
FIG. 2 is a drawing of a human heart illustrating the lead shown in FIG. 1 when fully implanted therewithin.
FIG. 3 is an elevational view of another prebent or preshaped lead made in accordance with this invention, useful for atrial pacing and shown in its molded, relaxed condition.
FIG. 4 is a drawing of human heart illustrating the lead of FIG. 3 in a fully implanted condition.
Figure 5:
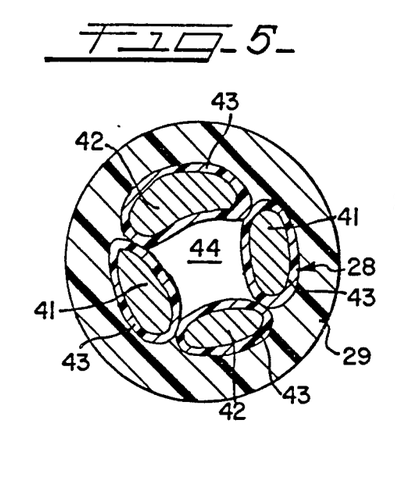
FIG. 5 is a transverse cross-sectional view along the line 5—5 of FIG. 1.
Figure 6:
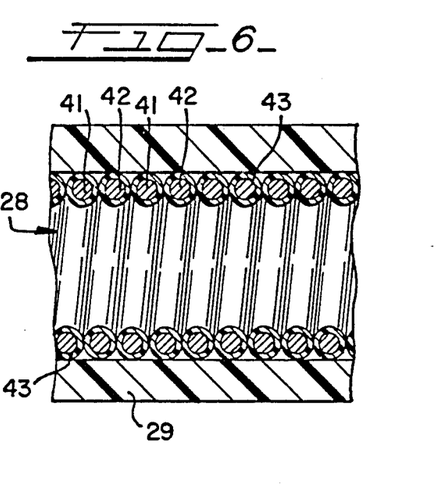
FIG. 6 is a longitudinal cross-sectional view along the line 6—6 of FIG. 1.
Figure 7:
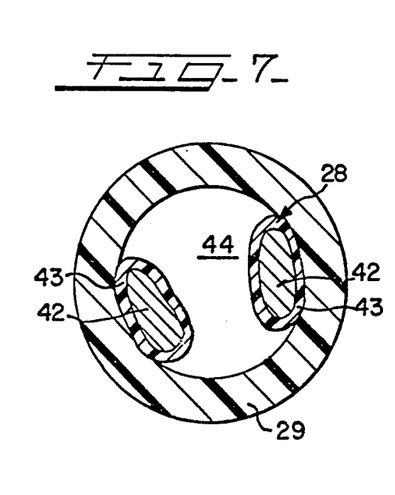
FIG. 7 is a transverse cross-sectional view along the line 7—7 of FIG. 1.
Figure 8:
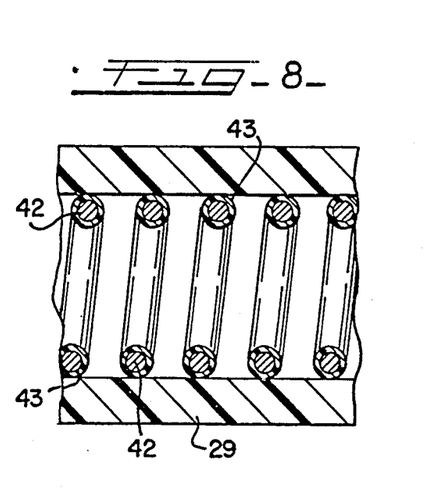
FIG. 8 is a longitudinal cross-sectional view along the line 8—8 of FIG. 1.
Figure 15:
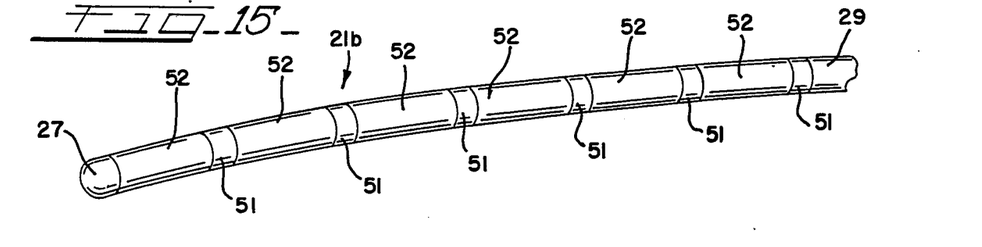
FIG. 15 is an elevational view, partially broken away, of another embodiment of a lead made in accordance with this invention, showing a lead having multiple, closely spaced, electrodes.

A lead made in accordance with this invention is generally designated as 21 in FIG. 1, as 21a in FIG. 3, and as 21b in FIG. 15. Lead 21 includes an unbranched, preshaped portion, generally designated as 22. Unbranched preshaped, prebent portion 22 includes one or more atrial electrodes 25 for the atrial portion 23 of the heart and one or more ventricular electrodes 26, one of which is often a tip electrode 27. Ring electrodes 51 are shown in FIG. 15. Each such electrode 25, 26, 27, 51, typically made of platinum, stainless steel, porous carbon or the like, is in electrical communication with one of the conductors of a multifilar coil 28, located within an elongated flexible insulating sheath 29. Multifilar coil 28 includes a plurality of coiled conductors that have low electrical resistance and are very flexible and fatigue resistant, such as tantalum wire or drawn braised strand silver coated Elgiloy wire having a diameter of about 0.003 inch to 0.005 inch.

Portion 22, which is located at the generally distal end portion of the lead 21 of the embodiment shown in FIGS. 1 and 2, is molded such that, when same is in its relaxed condition as illustrated in FIG. 1, this unbranched prebent portion 22 includes a number of consecutive curved sections that interact with each other and are shaped as an integral unit in order to achieve the advantageous properties such as being disposed toward self-seating during and after implantation within a human heart. These interacting consecutive curved sections of the unbranched prebent portion include an enhanced stiffness section 31 having a length and configuration designated as A in FIG. 1 and as A' in FIG. 3. This can be joined to an atrial section 32 at which each atrial electrode 25 is located. Enhanced stiffness section 31 and atrial section 32 combine to impart an overall tightly curved shape which is in the nature of a J-shaped atrial lead which can, if desired, have its portion that contacts the atrial portion 23 of the heart 24 take the form of a generally arcuate length that curves generally oppositely of the J-shaped portion and away from the atrial portion 23.

Located distally of the atrial section 32 of lead 21 shown in FIGS. 1 and 2 is an intermediate, generally S-shaped section 33 and a ventricular section 34 at which the ventricular electrode(s) 26, 27 are mounted, such combining to form an overall gradually curved S-shape. The overall tightly curved S-shape of the enhanced stiffness section 31 and the atrial section 32 combines with this overall gradually curved S-shape to form an unbranched prebent portion 22 that has the combined general configuration of two consecutive S-shaped curves. Preferably, all of the enhanced stiffness section 31, the atrial section 32, the intermediate S-shaped section 33, and the ventricular portion 34 each have substantially the same external diameter, the difference in stiffness between the enhanced stiffness section 31 and the rest of the lead 21 being brought about by the use of a sheath material at the enhanced stiffness section 31 that has a stiffness value greater than that of the rest of the sheath, which thus has a greater flexibility than the enhanced stiffness section 31.

A terminal assembly 36 of generally known construction is attached to the proximal end of each lead extension such as an atrial lead extension 37 and a ventricular lead extension 38. Each conductor of the multifilar coil 28 which is secured to and which terminates at an electrode 25, 26, 27 or 51 is included within the appropriate lead extension and is in electrical engagement with its terminal assembly 36. In an embodiment such as is illustrated in FIG. 3, only a single conductor wire need be used, such connecting the terminal assembly 36 with the atrial electrode 25. In accordance with conventional techniques, each terminal assembly 36 is provided for electrically connecting the lead to a suitable diagnostic device or pacemaker (not shown).

In this regard, it is important to accurately position the electrode(s) 25, 26, 27, 51. While these electrodes may be of a self-attachment type when long-term implantation is desired, for example by having a porous surface whereby tissue ingrowth serves to enhance holding of the electrodes, such ingrowth is somewhat gradual, and the electrodes are susceptible of movement until adequate ingrowth has been established. When provided, the unbranched preshaped, prebent portion 22 is useful to achieve self-seating of the electrodes where desired.

Figure 16:
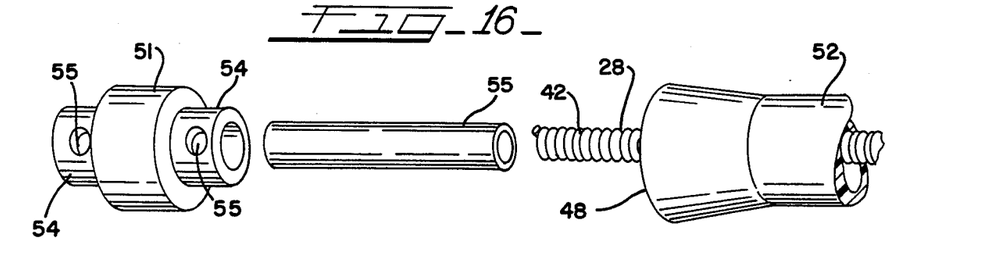
FIG. 16 is a perspective view of an initial step in the preferred method of assembling an electrode onto a lead in accordance with this invention.

Multifilar coil 28, as illustrated in FIGS. 5, 6, 7 and 8, has each of its individual coaxially wound coiled conductors, including atrial coil conductor(s) 41 and ventricular coil conductor(s) 42, encapsulated with an insulating coating 43, for example a polymer such as a polyimide. Four coil conductors are illustrated in FIG. 1, and it is to be understood that a lesser or greater number, typically as many as ten or more, coil conductors may be included; for example, seven are shown in FIGS. 15 and 16. A lumen 44 is substantially coaxial with the multifilar coil 28. Lumen 44 accommodates a stylet 45 which is inserted into the lead at the terminal assembly 36 and which can be passed therethrough.

With particular reference to the ventricular/atrial lead 21 of FIGS. 1 and 2, in order to effect its implantation in a typical surgical procedure, the lead 21 is passed through a vein so as to gain access to the superior vena cava 46 for subsequent access to the right atrium 23 and to the right ventricle 39. Typically, the surgeon gains access to a suitable vein such as a subclavian, cephalic or external jugular vein by surgical incision at a suitable location. In many instances, access to the vein at the surgical incision is enhanced by an introducer sheath or the like (not shown) in accordance with known techniques. The lead 21 is then passed through the introducer sheath and through the vein which opens into the superior vena cava 46.

During this passage through the vein, it is necessary to stiffen the lead 21 while also substantially straightening the preshaped or prebent portion 22. Such is accomplished by the insertion of the stylet 45 into the lumen 44 and into the ventricular section 34. With the stylet 45 thus inserted therewithin, the lead 21, after having been inserted through the appropriate vein to the superior vena cava 46, is advanced into the atrium 23. Stylet 45 is then partially withdrawn until distal portions of the prebent configuration reform to the extent needed to manipulate the lead 21 such that the ventricular section 34 and a portion of the intermediate, S-shaped section 33 enter the ventricle 39. At this point, the stylet 45 is typically again advanced to the ventricular section 34 which assists in positioning the lead into the ventricle 39 toward its seated location. When the lead 21 is appropriately thus positioned in the ventricle 39, the stylet 45 is withdrawn from the ventricular section 34 and from at least a portion of the intermediate, S-shaped section 33, permitting sections 33, 34 to substantially return to their respective preshaped configurations.

Stylet 45 is then further withdrawn from the atrial section 32 and from the enhanced stiffness section 31, at which time sections 31 and 32 generally return to their respective prebent configurations. At this stage, the lead 21 is further manipulated until the atrial section 32 gains access to and initially seats within the atrial portion 23. Stylet 45 is then removed completely, and the surgeon imparts some tension on the lead 21 in order to exert pressure on the atrial electrode(s) 25. Seating of the atrial section 32 within the atrium 23 may involve pushing, twisting and pulling movement of the lead 21 and typically results in a seated position at which the lead 21 is in slightly tensioned engagement with a wall of the superior vena cava 46 or closely spaced tissues, exemplary seatings in this regard being illustrated in FIG. 2 and in FIG. 4. At this stage, the lead 21 typically is secured at its exit from the vein, and the terminal assemblies 36 are connected to the pacing device. Implantation of the lead 21a of FIGS. 3 and 4 is accomplished in much the same manner except, of course, manipulation of ventricular sections is not carried out.

The elongated flexible insulating sheath 29 of the lead 21, 21a, 21b is molded of a body-compatible material that is relatively strong yet somewhat pliable and soft, while being heat and/or pressure formable and bendable so as to allow shaping of the assembled lead. Preferred materials include thermoplastic polymers such as polyurethanes, in particular Pellethane D-55 and D-75 (Upjohn). In accordance with a preferred aspect of this invention, the enhanced stiffness section 31 is made of substantially the same material as the rest of the sheath 29, except the material (for example Pellethane D-75) of enhanced stiffness section 31 is somewhat stiffer than the rest of the sheath 29 (for example Pellethane D-55) when the lead is at body temperature. A preferred arrangement in this regard is to mold the entire sheath 29 of a polyurethane, except that enhanced stiffness section 31 thereof is made of a particular polyurethane that is formulated to exhibit somewhat greater stiffness than the polyurethane out of which the remainder of the sheath 29 is made. The entire sheath 29 can have the same diameter, which may be as small as French 5 (0.066 inch or 1.67 mm) or less. Other sizes include outer diameters of between 0.045 inch and 0.075 inch.

When included, the intermediate S-shaped section 33 and the ventricular section 34 are typically more flexible than the enhanced stiffness section 31 and the atrial section 32 so as to avoid the development of excessive column-type forces. This is achieved in part because of the gradually curving shape of sections 33 and 34 and also by virtue of the fact that each atrial coil conductor 41 terminates at an atrial electrode 25, with the result that there are fewer coil conductors in the multifilar coil 28 within the sections 33 and 34 than within the rest of the lead 21, thereby reducing the resistance to bending of the sections 33 and 34 when compared with sections 31 and 32.

Anchor tines 35 may be provided. Especially suitable are very thin polymeric tines positioned on generally opposite sides of the ventricular section 34. Exemplary tines are made of 0.001 to 0.002 inch thick polyurethane. Anchor tines 35 of this type securely stabilize the ventricular electrodes 26, 27 in position while allowing removal when desired in the future by twisting the lead 21 thereby winding the anchor tines 35 around the ventricular section 34. This twisting procedure generally pulls the anchor tines 35 from their embedded location. This approach is also very useful for eliminating tricuspid valve entrapment and position changing problems, and it allows for entry of a tined lead through relatively small entrance vessels and introducing sheaths.

FIGS. 9 through 14 generally illustrate one approach that can be taken to practice the present method in order to join the various sections of the lead, these drawings particularly illustrating the situation when such joining includes the incorporation of a ring electrode (such as 25, 26, 51) thereat, and it is to be understood that substantially the same assembly arrangement is suitable for joining the various sections together at a location that does not include a ring electrode. The assembly illustrated in the drawings is that of the atrial ring electrode 25, the enhanced stiffness section 31, and the atrial section 32.

Figure 9:
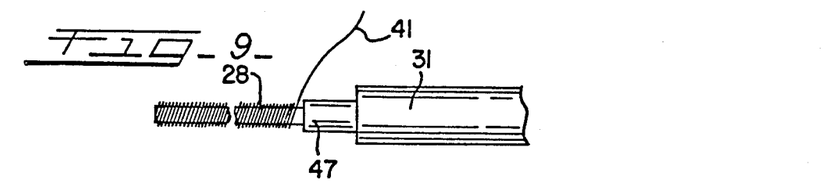
FIGS. 9, 10, 11, 12 and 13 are elevational views of sequential steps in one method for the assembly of an electrode onto a lead in accordance with this invention.
Figure 10:
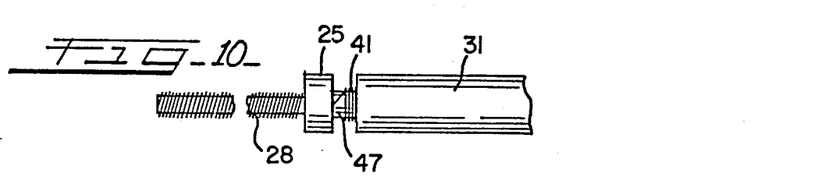

Referring to FIG. 9, a length of tubing adequate to form the atrial section 31 is positioned over the multifilar coil 28 with a close fitting mandrel in place, and an annular step 47 having an axial length greater than the axial length of the electrode 25 is formed at the end of the atrial section 31. Annular step 47 provides an annular sheath that is preferably formed by using a heated die which imparts pressure and an elevated temperature to an end of the atrial section 31 that is adequate to reform the material into the coil thereof so that the annular step 47 forms an annular sheath that is radially recessed and has an outer diameter that is less than that of the atrial section 31. After the formation of the radially recessed annular sheath or annular step 47, the distal end of an atrial coil conductor 41 is uncoiled and stripped so as to remove its insulating coating 43. This permits the thus uninsulated section of the conductor 41 to be wrapped around the annular step 47. Preferably, the annular step 47 and wrapped conductor 41 are then coated with a conductive epoxy material, primarily to enhance the electrical contact between the conductor 41 and the electrode 25 but also to provide a moisture seal. The ring electrode 25 is then assembled over the annular step 47, wrapped conductor 41, and epoxy conductive material until same abuts with the unstepped portion of the atrial section 31, such movement being illustrated between FIGS. 10 and 11.

Figure 11:
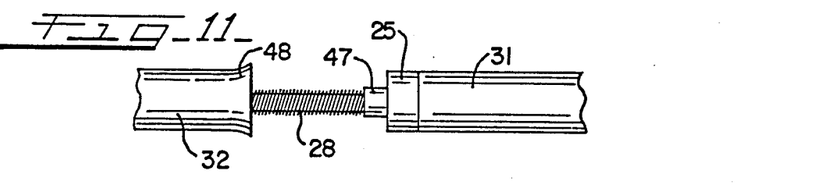
Figure 12:
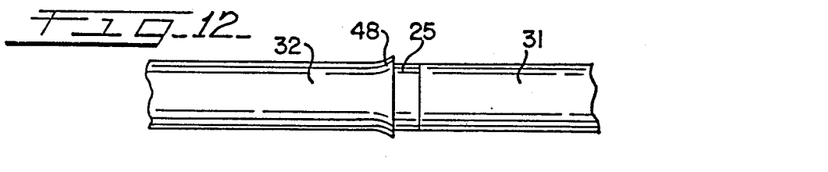
Figure 13:
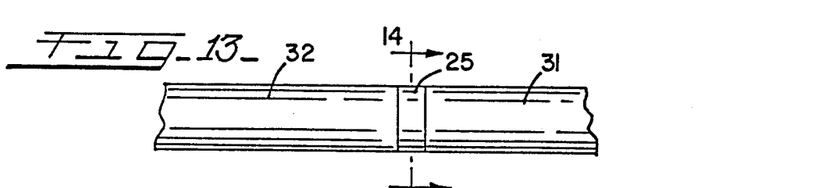
Figure 14:
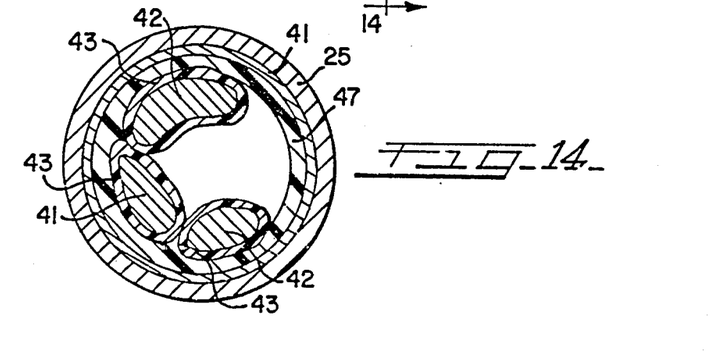
FIG. 14 is a transverse cross-sectional view along the line 14—14 of FIG. 13.

Next, as illustrated between FIGS. 11 and 12, the less stiff section 32, preferably having a hot-worked or cold-worked flared end 48, is assembled over the multifilar coil 28 until the flared end 48 engages and butts against the free edge of the electrode 25, such also covering the portion of the annular step 47 and conductor 41 that extends beyond the electrode 25. The flared end 48 of this assembly is then reformed and fused to annular step 47, typically by the application of heat and pressure by a suitable die arrangement, to the fully assembled configuration illustrated in FIGS. 13 and 14, such that the external surface of the electrode 25 is generally flush with both the atrial section 32 and the enhanced stiffness section 31.

FIGS. 16 through 21 generally illustrate the preferred approach in practicing the method of the present invention in order to join together the various sections of the lead, these drawings particularly illustrating the situation when such joining includes the incorporation of a ring electrode member 51 thereat, and it is to be understood that a similar assembly arrangement could be suitable for joining the various sections together at a location that does not include a ring electrode. The assembly illustrated in the drawing is one including a ring electrode member 51 having an annular external electrode surface, connected to a sheath section 52 of the insulating sheath 29.

Figure 17:
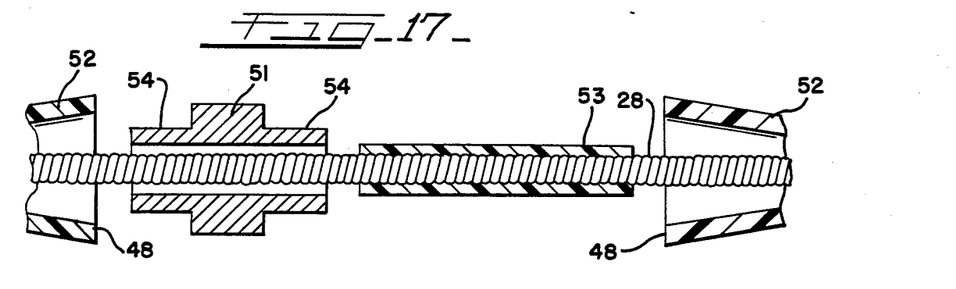
FIG. 17 is a longitudinal cross-sectional view through an assembly as generally illustrated in FIG. 16.

Referring to FIG. 16, a sheath section 52 is positioned over the multifilar coil 28, preferably while it is supported by a mandrel. Coil 28 can have an outer diameter on the order of 0.035 inches. The end of the sheath section 52 for engagement with the ring electrode 51 has a flared end 48. A radially recessed annular sheath 53 is slid over the multifilar coil 28 generally adjacent to the flared portion 48 of the sheath section 52. Ring electrode member 51 is likewise positioned over the multifilar coil 28, as is another sheath section 52 having a flared end directed toward the electrode 51. FIG. 17 shows each of these components in its orientation for assembly.

Illustrated ring electrode member 51 includes an annular flange 54 on opposing axial ends of an external annular electrode surface. Preferably each such flange 54 includes an opening 55 therethrough. The opening illustrated is generally circular, but other openings are suitable, such as circumferentially oriented slits. A plurality of such openings 55 may be provided as desired; for example, four openings 55 can be provided on each flange 54 at locations generally evenly spaced around the flange 54.

Figure 18:
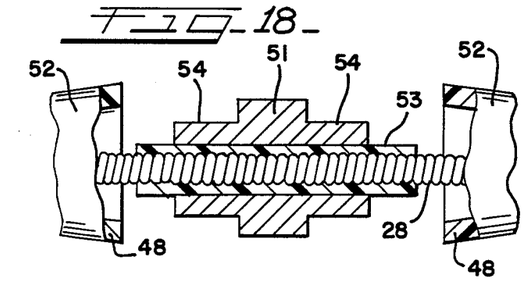
FIG. 18 is a longitudinal cross-sectional view illustrating an assembly step subsequent to that shown in FIG. 17.

As illustrated in FIG. 18, the ring electrode member 51 is then generally centered along the length of the radially recessed annular sheath 53 which forms oppositely directed annular steps projecting beyond each flange 54. One coil 41 of the multifilar coil 28 is uncoiled and, if necessary, a portion thereof is cut off and discarded. The end of the uncoiled conductor 41 is stripped of its insulating coating. The uncoiled length is wound first around an end portion of the annular step formed by the radially recessed annular sheath 53 and then around the flange 54 of the electrode member 51, after which a spot weld 56 or the like is formed so as to electrically communicate the stripped end of the conductor 41 with the flange 54 of the electrode member 51. Spot welding typically is suitable because it does not generate excessive heat which could lead to melting, deformation or other damaging of the assembly. Procedures such as laser welding or exceptionally fast braising could be suitable in this regard. This results in an assembly at a stage that is generally illustrated in FIG. 19.

Next, the sheath sections 52 are moved toward each other until each flared end portion 48 generally overlies an annular flange 54. Each sheath section 52 is then heat-reformed, typically by the application of heat and pressure through a suitable die arrangement, in order to move from the condition illustrated in FIG. 20 to fully assembled condition illustrated in FIG. 21. Generally, the formed assembly is structured such that each sheath section 52 is substantially isodiametric with and buts up against the external electrode surface of the electrode member 51. Preferably, this heat reforming also accomplishes a flow of the thermoplastic material of each sheath section 52 through each opening 55 and onto the surface of the radially recessed annular sheath 53 in order to thereby form a fused assembly of the sheath section 52 to the annular sheath 53 through each opening 55 in the flanges 54 of the electrode member 51. In instances where a plurality of electrode assemblies are to be provided in generally close location with respect to each other, such as illustrated in FIG. 15, this heat reforming can be simultaneously accomplished for multiple electrode assemblies in order to enhance the efficiency of the procedure.

Figure 19:
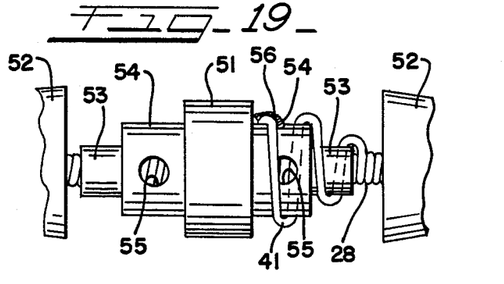
FIG. 19 is an elevational view illustrating an assembly step subsequent to that shown in FIG. 18.
Figure 20:
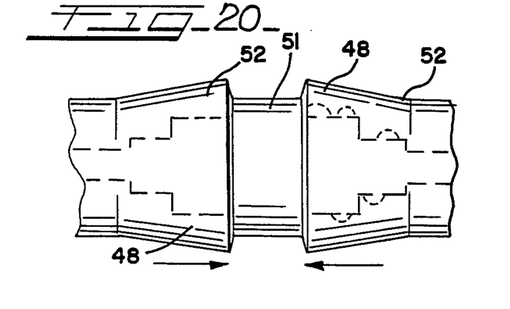
FIG. 20 is an elevational view showing an assembly step subsequent to that of FIG. 19.
Figure 21:
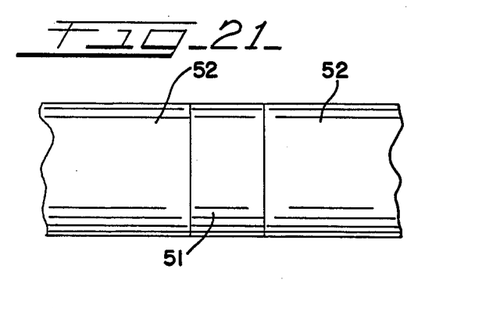
FIG. 21 is an elevational view illustrating the completed electrode assembly made according to FIGS. 16 through 20.

The winding of the strand conductor 41 in the manner generally shown in FIG. 19 provides a substantially spring-like structure. A structure of this type enhances the strain relief available when the assembly is bent or flexed during implantation or subsequent use. It also provides an extended fluid path in order to further ensure against fluid leakage from outside of the assembly. Additionally, the secure assembly provided is especially resistant to splitting or deterioration upon being subjected to the flexing and bending that can be expected during use of such devices, whereby a fluid tight and mechanically strong joint is formed.

It will be apparent to those skilled in the art that various modifications are possible without departing from the spirit and scope of this invention; accordingly, this invention is to be construed only by the appended claims.

We claim:
1. A method for constructing an implantable lead, comprising:
positioning a first section of flexible insulating polymeric sheath over a coiled conductor member having an insulator coating;
providing a short annular sheath over said coiled conductor member, said short annular sheath being radially recessed with respect to and axially extending beyond said first insulating sheath section;
uncoiling a length of said coiled conductor member and removing a portion of its insulator coating to form a free conductor length having an uninsulated portion;
wrapping at least a portion of said free conductor length generally around at least a portion of said short annular sheath;

engaging an electrode member into electrical communication with said uninsulated portion of said free conductor length;

butting together said electrode member and said first section of flexible insulating polymeric sheath until one axial face of said electrode member engages an axial face of said first section of insulating polymeric sheath; and sliding a second section of flexible insulating polymeric sheath over said coiled conductor member and butting together said electrode member and said second section of flexible insulating polymeric sheath until another axial face of said electrode member engages an axial face of said second section of insulating polymeric sheath.

2. The method according to claim 1, wherein said coiled conductor member is a multifilar coil and a plurality of electrode members are provided, and wherein said method includes a plurality of said uncoiling and wrapping steps, followed by engaging each uninsulated portion of each free conductor length with one of said electrode members, and said butting and sliding steps are repeated to provide a structure wherein the electrode members are insulated from each other.

3. The method according to claim 1, further including circumferentially flaring an end portion of said second section of flexible insulating polymeric sheath in order to form a flared end portion thereof prior to said sliding step, and subsequent to said sliding step reforming said flared end portion so as to be substantially isodiametric with the remainder of said second section and with the surface of said electrode member.

4. The method according to claim 1, further including circumferentially flaring an end portion of said first section of flexible insulating polymeric sheath in order to form a flared end portion thereof prior to said positioning step, and subsequent to said butting step reforming said flared end portion so as to be substantially isodiametric with the remainder of said first section and with the surface of said electrode member.

5. The method according to claim 3, further including providing an axially extending flange of said electrode member, and forming at least one opening through said flange, whereby during said reforming step polymeric material from said second section of insulating sheath is joined with polymeric material from said radially recessed short annular sheath.

6. The method according to claim 4, further including providing an axially extending flange of said electrode member and forming at least one opening through said flange, whereby during said reforming step polymeric material from said first section of insulating sheath is joined with polymeric material from said radially recessed short annular sheath.

7. The method according to claim 1, wherein said engaging step includes spot welding said uninsulated portion of the free conductor length onto an axially extending flange of said electrode member.

8. The method according to claim 1, wherein said step of providing a radially recessed short annular sheath over said coiled conductor member includes imparting heat and pressure to an end portion of said first section of flexible insulating polymeric sheath to the extent that the inner surface of the thus formed radially recessed short annular sheath engages and generally conforms to the external shape of said coiled conductor member.

9. The method according to claim 1, wherein said step of providing a radially recessed short annular sheath over said coiled conductor member includes positioning a polymeric tube over said coiled conductor member and under said electrode member, which polymeric tube has an outside diameter less than that of the inside diameter of the first section of flexible insulating sheath.

10. The method according to claim 9, wherein said polymeric tube is shaped so as to have at least a portion of its inside surface engaged with and in substantial shape conformity with the outside surface of the coiled conductor member.

11. A method for constructing an implantable lead, comprising:

positioning a first section of flexible insulating polymeric sheath over a coiled conductor member having an insulator coating;

locating a short annular sheath polymeric tube over said coiled conductor member, said short annular sheath polymeric tube having an outside diameter less than that of said first section of flexible insulating polymeric sheath;

moving onto said coiled conductor member an electrode member having an electrode surface and an axially directed flange that is radially recessed with respect to the electrode surface, said electrode member having an axial bore with an internal diameter greater than the external diameter of said short annular sheath polymeric tube, and said axially directed flange having an outside diameter no greater than the greatest inside diameter of the first section of flexible insulating sheath;

imparting relative sliding movement between said electrode member and said short annular sheath polymeric tube;

uncoiling a length of said coiled conductor member and removing a portion of its insulation to form a free conductor length having an uninsulated portion;

wrapping at least a portion of said free conductor length generally around at least a portion of said electrode flange;

sliding an end portion of said first section of flexible insulating polymeric sheath over said wrapped conductor length and heat-reforming said end portion of the first section until same is secured to and is substantially isodiametric with the remainder of said first section and with the electrode surface of the electrode member; and sliding a second section of flexible insulating polymeric sheath over said coiled conductor member and butting together said electrode member and said second section of flexible insulating polymeric sheath.

12. The method according to claim 11, wherein said electrode member includes a second axially directed flange that is radially recessed with respect to said electrode surface and that extends in a direction opposite to that of said first flange, said step of moving the electrode member with respect to the short annular sheath polymeric tube includes positioning said short annular sheath polymeric tube under said second flange, and said method further includes heat-reforming an end portion of the second section of flexible insulating polymeric sheath until same is secured to and is substantially isodiametric with the remainder of said second section and with the electrode surface of the electrode member.

13. The method according to claim 11, further including providing at least one opening through said flange portion of the electrode member, and said end portion heat-reforming step includes joining, through said opening, an internal portion of said first section of flexible insulating sheath with an external portion of said short annular sheath polymeric tube.

14. The method according to claim 12, further including forming at least one opening through said second flange portion of the electrode member, and said end portion heat-reforming step includes joining, through said opening, an internal portion of said second section of flexible insulating sheath with an external portion of said short annular sheath polymeric tube.

15. The method according to claim 11, further including flaring said end portion of the first section of flexible insulating polymeric sheath, and said heat-reforming step includes reforming said flared end portion to said substantially isodiametric condition.

16. The method according to claim 12, further including, prior to said second section sliding and butting step, flaring said end portion of the second section of flexible polymeric insulating sheath, and said step of heat-reforming the second section includes reforming said flared end portion to said substantially isodiametric condition.

17. A method for constructing an implantable lead, comprising:
selecting a length of multifilar coil having a plurality of coaxially wound coil conductors alternately interwound with each other, each said conductor being insulated;
positioning a first section of flexible insulating polymeric sheath over a length of said multifilar coil;
forming an annular, radially recessed step at an end of said first sheath section;
uncoiling a length of one of said coil conductors and removing at least a portion of its insulation to form a free conductor length;
wrapping said free conductor length generally around said annular, radially recessed step;
assembling an electrode member over said annular, radially recessed step and over said wrapped conductor length until said electrode member substantially covers at least said uninsulated portion of the wrapped conductor length and the innermost length of said recessed step and until the leading end of the first section of insulating polymeric sheath generally butts against said electrode member; and
sliding a second section of flexible insulating polymeric sheath over said multifilar coil until its leading end generally butts against said electrode member.

18. The method according to claim 17, further including:
forming an annular, radially recessed step at an opposite end of said second sheath section; and
sliding a third section of flexible insulating sheath over said multifilar coil until its leading end circumferentially engages and substantially fully covers the annular radially recessed step of said second sheath section.

19. The method according to claim 17, further including:
forming a second annular, radially recessed step on an opposite end of said second sheath section;
uncoiling a length of another of said coil conductors and removing at least a portion of its insulation to form a second free conductor length;
wrapping said second free conductor length generally around said second annular, radially recessed step;
assembling another electrode member over said second recessed step and over said second wrapped conductor length until said another electrode member substantially covers at least said uninsulated portion of the second wrapped conductor length and the innermost length of said second recessed step and until the leading end of the second section of insulating polymeric sheath generally butts against said another electrode member; and
sliding a third section of flexible insulating polymeric sheath over said multifilar coil until its leading end generally butts against said another electrode member.

20. The method according to claim 19, wherein one of said electrodes is a ventricular electrode and another of said electrodes is an atrial electrode.

21. The method according to claim 17, wherein said forming of an annular, radially recessed step includes imparting heat and pressure to a length of said sheath section.

22. The method according to claim 17, wherein said annular, radially recessed step is formed to have a length greater than the axial length of the electrode.

23. The method according to claim 17, wherein said second section sliding step is followed by imparting heat and pressure to the leading end of the second sheath section.

* * * * *